United States Patent [19]

Kirino et al.

[11] 4,288,244
[45] Sep. 8, 1981

[54] N-BENZYLHALOACETAMIDE DERIVATIVES, AND THEIR PRODUCTION AND USE

[75] Inventors: Osamu Kirino, Ashiya; Shunichi Hashimoto, Sonchigashimachi; Hiroshi Matsumoto, Takarazuka; Hiromichi Oshio, Osaka, all of Japan

[73] Assignee: Sumitomo Chemical Company, Limited, Osaka, Japan

[21] Appl. No.: 75,705

[22] Filed: Sep. 14, 1979

[30] Foreign Application Priority Data

Sep. 19, 1978 [JP] Japan .................. 53/115588
Nov. 10, 1978 [JP] Japan .................. 53/139069
Nov. 14, 1978 [JP] Japan .................. 53/140800

[51] Int. Cl.³ .................. A01N 37/18; C07C 103/127
[52] U.S. Cl. .................. 71/118; 564/212
[58] Field of Search .............. 71/118, 92; 260/558 R, 260/559 R, 561 HL, 562 B

[56] References Cited

U.S. PATENT DOCUMENTS

| Re. 26,961 | 10/1970 | Hamm et al. | 71/118 |
| 2,864,679 | 12/1958 | Hamm et al. | 71/118 |
| 3,498,781 | 3/1970 | Buntin | 71/118 |
| 3,644,521 | 2/1972 | Buntin | 71/118 |
| 3,839,446 | 10/1974 | Teach | 71/118 |
| 3,871,865 | 3/1975 | Teach | 71/118 |
| 4,021,224 | 5/1977 | Pallos et al. | 71/118 |
| 4,195,036 | 3/1980 | Gozzo et al. | 71/118 |

OTHER PUBLICATIONS

Homeyer et al., J.A.C.S. vol. 55, pp. 4209–4214 (1933).

*Primary Examiner*—Glennon H. Hollrah
*Attorney, Agent, or Firm*—Birch, Stewart, Kolasch & Birch

[57] ABSTRACT

A compound of the formula:

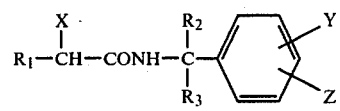

wherein $R_1$ is a $C_4$-$C_7$ tertiary alkyl group, X is a halogen atom, $R_2$ is a methyl group or an ethyl group, $R_3$ is a methyl group or an ethyl group, or when $R_2$ and $R_3$ are taken together, they represent a $C_2$-$C_5$ alkylene group, and Y and Z, which may be the same or different, are each a hydrogen atom, a halogen atom, a methyl group or a methoxy group, which is useful as a herbicide.

13 Claims, No Drawings

N-BENZYLHALOACETAMIDE DERIVATIVES, AND THEIR PRODUCTION AND USE

The present invention relates to N-benzylhaloacetamide derivatives, and their production and use. More particularly, it relates to N-benzylhaloacetamide derivatives and herbicidal compositions comprising them, and their preparation processes.

The said N-benzylhaloacetamide derivatives are representable by the formula:

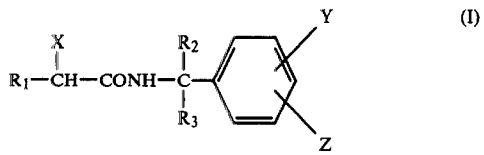

wherein $R_1$ is a $C_4$–$C_7$ tertiary alkyl group, X is a halogen atom, $R_2$ is a methyl group or an ethyl group, $R_3$ is a methyl group or an ethyl group, or when $R_2$ and $R_3$ are taken together, they represent a $C_2$–$C_5$ alkylene group, and Y and Z, which may be the same or different, are each a hydrogen atom, a halogen atom, a methyl group or a methoxy group.

The term "halogen atom" as hereinabove used is intended to mean chlorine, bromine, fluorine and iodine, inclusively.

As the result of an extensive study, it has been found that the N-benzylhaloacetamide derivatives (I) have a strong herbicidal activity against a wide variety of weeds. For instance, they can exert a notable controlling or eradicating activity on the following annual and perennial weeds by pre-emergence soil treatment or post-emergence foliar or soil treatments: Gramineae weeds such as barnyard-grass (*Echinochloa crus-galli*), large crabgrass (*Digitaria sanguinalis*), green foxtail (*Setaria viridis*), Cyperaceae weeds such as yellow nutsedge (*Cyperus esculentus*), nutsedge sp. (*Cyperus difformis*), purple nutsedge (*Cyperus rotundus*), *Scirpus Hotarui*, slender spikerush (*Eleocharis acicularis*), *Cyperus serotinus* and *Eleocharis kuroguwai*, Amaranthaceae weeds such as redroot pigweed (*Amaranthus retroflexus*), Chenopodiaceae weeds such as common lambsquarters (*Chenopodium album*), Polygonaceae such as ladysthumb (*Polygonum persicaria*) and curlydock (*Rumex japonicus*), Pontederiaceae such as *Monochoria vaginalis*, Scrophulariaceae such as false pimpernel (*Lindernia pyxidaria*), Alismataceae such as arrowhead (*Sagittaria pygmaea*), Compositae such as dandelion (*Taraxacum officinale*), Oxalidaceae such as woodsorrel (*Oxalis corniculata*), etc. Thus, their herbicidal activity is effective in controlling and eradicating not only field weeds but also paddy field weeds.

Advantageously, the N-benzylhaloacetamide derivatives (I) do not produce any injury on various crop plants such as rice, soybean, cotton, corn, peanut, sunflower, rape and potato and numerous vegetables such as lettuce, cabbage, tomato, cucumber and carrot.

Accordingly, the N-benzylhaloacetamide derivatives (I) are useful as herbicides applicable for field crops and vegetables as well as paddy rice. They are also useful as herbicides to be employed for orchard, lawn, pasture, tea garden, mulberry field, rubber plantation, forest, etc. applications.

Japanese Patent Publication (unexamined) No. 88228/1973 and U.S. Pat. No. 3,498,781 disclose some pivalic acid amide derivatives, which are somewhat similar to the N-benzylhaloacetamide derivatives (I) in chemical structure and have a herbicidal activity. However, the herbicidal activity of the N-benzylhaloacetamide derivatives (I) is generally more excellent than that of the pivalic acid amide derivatives. It is particularly notable that, in comparison with the pivalic acid amide derivatives, the N-benzylhaloacetamide derivatives (I) exert an extremely high herbicidal effect on annular and perennial weeds in paddy fields without any phytotoxicity on rice plants. Further, the N-benzylhaloacetamide derivatives (I) are quite characteristic in being highly effective for controlling or eradicating perennial Cyperaceae weeds.

The N-benzylhaloacetamide derivatives (I) can be produced by reacting a haloacetic acid of the formula:

wherein $R_1$ and X are each as defined above, or its reactive derivative with a benzylamine compound of the formula:

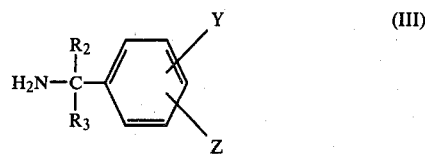

wherein $R_2$, $R_3$, Y and Z are each as defined above.

The haloacetic acid (II) or its reactive derivative may be synthesized, for instance, by the method as disclosed in J. Am. Chem. Soc., 55, 4209 (1933). The benzylamine compound (III) is obtainable, for instance, by the method as disclosed in J. Am. Chem. Soc., 71, 3929 (1949).

For the reaction, the haloacetic acid (II) or its reactive derivative and the benzylamine compound (III) may be used in an equivalent ratio of 0.4 to 1.5:1, preferably 0.5 to 1.1:1. The reaction may be carried out in the presence or absence of an inert solvent. Examples of the inert solvent are hydrocarbons (e.g. benzene, toluene, xylene), halogenated hydrocarbons (e.g. chlorobenzene, methylene chloride, chloroform, carbon tetrachloride), ethers (e.g. diisopropyl ether, tetrahydrofuran, dioxane), alcohols (e.g. methanol, ethanol, isopropanol), ketones (e.g. acetone, methylethylketone, methylisobutylketone), esters (e.g. ethyl acetate), nitriles (e.g. acetonitrile), dimethylsulfoxide, dimethylformamide, water, etc. Among them, particularly preferred is benzene. The reaction may be carried out within a wide range of temperature from the freezing point to the boiling point of the solvent, preferably from 0° C. to the boiling temperature of the solvent. If necessary, cooling or heating may be adopted.

As the haloacetic acid (II) or its reactive derivative, there may be used the free acid, acid anhydride, acid chloride, acid bromide, acid ester, etc. Depending upon the kind of the reactive derivative, an appropriate reaction aid such as a condensing agent, a dehydrating agent, an acid-eliminating agent or a catalyst may be employed in the reaction. In case of the free acid, dicyclohexylcarbodiimide, phosphorus pentachloride, phosphorus trichloride, phosphorus tribromide, thionyl chloride, sodium hydroxide, potassium hydroxide, sodium methoxide, sodium ethoxide, triethylamine, pyridine, quinoline, isoquinoline, N,N-dimethylaniline, N,N-diethylaniline, N-methylmorpholine, etc. are examples of the reaction aid. In case of the acid chloride or acid bromide, sodium hydroxide, potassium hydroxide, sodium methoxide, sodium ethoxide, triethylamine, pyridine, quinoline, isoquinoline, N,N-dimethylaniline, N,N-diethylaniline, N-methylmorpholine, sodium acetate, etc., preferably triethylamine, are usable as the reaction aid. When the reaction aid is employed, its amount may be from a catalytic amount to 1.5 equivalents, preferably from 0.95 to 1.1 equivalents with respect to the material to be eliminated from the starting compounds as the result of the reaction.

The recovery of the reaction product from the reaction mixture may be carried out in a per se conventional manner. For instance, the reaction mixture is filtered and/or washed with water, followed by distillation for removal of the solvent to give the reaction product, i.e. the N-benzylhaloacetamide derivative (I). When desired, this reaction product may be purified by a per se conventional procedure such as recrystallization from an appropriate solvent such as benzene, toluene, n-hexane, methanol, ethanol, chloroform or methylisobutylketone.

The thus produced N-benzylhaloacetamide derivative (I) has an asymmetric carbon atom, and therefore its optical isomers are present. Irrespective of the racemic mixture or the optical isomer, the N-benzylhaloacetamide derivative (I) is usable as a herbicide in the present invention.

Practical embodiments of the preparation of the N-benzylhaloacetamide derivatives (I) are illustratively shown in the following examples.

EXAMPLE 1

Into a 200 ml four-necked flask, there were charged toluene (100 ml), $\alpha,\alpha$-dimethylbenzylamine (9 g) and pyridine (5.8 g), and $\alpha$-chloro-tert-butylacetyl chloride (11.3 g) was dropwise added thereto while stirring at room temperature. Stirring was continued for 3 hours. The reaction mixture was washed with water to remove pyridine hydrochloride. After the toluene layer was dried over anhydrous sodium sulfate, the solvent was distilled off under reduced pressure. The obtained residue was recrystallized from ethanol to give 15.8 g of N-($\alpha,\alpha$-dimethylbenzyl)-$\alpha$-chloro-tert-butylacetamide. M.P., 159°–160° C.

Elementary analysis: Calcd.: C, 67.28%; H, 8.28%; N, 5.23%; Cl, 13.24%. Found: C, 67.35%; H, 8.40%; N, 5.11 %; Cl,13.37%.

EXAMPLE 2

(1) Into a 200 ml four necked flask, there were charged benzene (100 ml), $\alpha,\alpha$-dimethylbenzylamine (9 g) and triethylamine (7.4 g), and $\alpha$-bromo-tert-butylacetyl chloride (14.5 g) was dropwise added thereto while stirring at room temperature. Stirring was continued for 3 hours. The reaction mixture was washed with water to remove triethylamine hydrochloride. After the benzene layer was dried over anhydrous sodium sulfate, the solvent was distilled off under reduced pressure. The obtained residue was recrystallized from ethanol to give 15.3 g of N-($\alpha,\alpha$-dimethylbenzyl)-$\alpha$-bromo-tert-butylacetamide. M.P., 182°–183° C.

Elementary analysis: Calcd.: C, 57.70%; H, 7.10%; N, 4.49%; Br, 25.59%. Found: C, 57.87%; H, 7.20%; N, 4.59%; Br, 25.56%.

(2) Into a 500 ml four-necked flask, there were charged methylisobutylketone (150 ml), $\alpha,\alpha$-dimethylbenzylamine (33.8 g) and triethylamine (27.8 g), and $\alpha$-bromo-tert-butylacetylbromide (64.5 g) was dropwise added thereto while stirring at room temperature. Stirring was continued for 3 hours. After completion of the reaction, water (200 ml) was added thereto and the reaction mixture was gradually heated to remove methylisobutylketone, followed by cooling at room temperature. The precipitated crystals were filtered, washed with water, dried and recrystallized from ethanol to give N-($\alpha,\alpha$-dimethylbenzyl)-$\alpha$-bromo-tert-butylacetamide (61.5 g).

(3) Into a 200 ml four-necked flask, there were charged $\alpha$-bromo-tert-butylacetic acid (9.8 g) and benzene (50 ml), and pyridine (50 ml) and $\alpha,\alpha$-dimethylbenzylamine (6.9 g) were dropwise added thereto while stirring at room temperature. Dicyclohexylcarbodiimide (10.8 g) was further added thereto, and the reaction was continued at 60°–70° C. for 6 hours, followed by cooling. The solvent was distilled off under reduced pressure, and the residue was extracted with hot benzene. The benzene extract was concentrated by distillation, and the residue was recrystallized from ethanol to give N-($\alpha,\alpha$-dimethylbenzyl)-$\alpha$-bromo-tert-butylacetamide (10.8 g).

EXAMPLE 3

Into a 200 ml four-necked flask, there were charged benzene (100 ml), $\alpha,\alpha$-dimethylbenzylamine (9 g) and triethylamine (7.4 g), and $\alpha$-bromo-tert-amylacetyl chloride (15.5 g) was dropwise added thereto while stirring at room temperature. Stirring was continued for 3 hours. After completion of the reaction, the reaction mixture was washed with water to remove triethylamine hydrochloride. After the benzene layer was dried over anhydrous sodium sulfate, the solvent was distilled off under reduced pressure. The residue was recrystallized from ethanol to give 15.8 g of N-($\alpha,\alpha$-dimethylbenzyl)-$\alpha$-bromo-tert-amylacetamide. M.P., 136°–137° C.

Elementary analysis: Calcd.: C, 58.90%; H, 7.41%; N, 4.29%; Br, 24.49%. Found: C, 58.88%; H, 7.65%; N, 4.28%; Br, 24.44%.

EXAMPLE 4

Into a 200 ml four-necked flask, there were charged benzene (150 ml), $\alpha,\alpha,2$-trimethylbenzylamine (7.5 g) and triethylamine (6 g), and $\alpha$-bromo-tert-butylacetyl chloride (10.2 g) was dropwise added thereto while stirring at room temperature. Stirring was continued for 3 hours. After completion of the reaction, the reaction mixture was washed with water to remove triethylamine hydrochloride. The benzene layer was dried over anhydrous sodium sulfate, and the solvent was distilled off under reduced pressure. The residue was recrystallized from ethanol to give 13.8 g of N-($\alpha,\alpha,2$-trimethylbenzyl)-$\alpha$-bromo-tert-butylacetamide. M.P., 166.5°–168° C.

Elementary analysis: Calcd.: C, 58.90%; H, 7.41%; N, 4.29%; Br, 24.49%. Found: C, 59.16%; H, 7.43%; N, 4.33%, Br, 24.50%.

EXAMPLE 5

Into a 200 ml four-necked flask, there were charged benzene (100 ml), 1-phenylcyclopropylamine (8.9 g) and triethylamine (7.4 g), and $\alpha$-bromo-tert-butylacetyl chloride (14.5 g) was dropwise added thereto while stirring at room temperature. Stirring was continued for 3 hours. After completion of the reaction, the reaction mixture was washed with water to remove triethylamine hydrochloride. The benzene layer was dried over anhydrous sodium sulfate, and the solvent was distilled off under reduced pressure. The obtained residue was recrystallized from ethanol to give 14.8 g of N-(1-phenylcyclopropyl)-α-bromo-tert-butylacetamide. M.P., 161°–162.5° C.

Elementary analysis: Calcd.: C, 58.07%; H, 6.50%; N, 4.51%; Br, 25.76%. Found: C, 58.24%; H, 6.73%; N, 4.50%, Br, 25.74%.

In the same manner as above, there can be produced other N-benzylhaloacetamide derivatives (I), of which some specific examples will be shown in Table 1 but without any intention to limit the scope of the invention thereto:

TABLE 1

$$R_1-CH(X)-CONH-C(R_2)(R_3)-C_6H_3(Y)(Z)$$

| Compound No. | $R_1$ | X | $R_2$ | $R_3$ | Y | Z | Melting point (°C.) | | C | H | N | Halogen |
|---|---|---|---|---|---|---|---|---|---|---|---|---|
| 1 | t-C$_4$H$_9$ | Cl | CH$_3$ | CH$_3$ | H | H | 159–160 | Calcd. | 67.28 | 8.28 | 5.23 | 13.24(Cl) |
| | | | | | | | | Found | 67.35 | 8.40 | 5.11 | 13.37(Cl) |
| 2 | t-C$_4$H$_9$ | Cl | CH$_3$ | CH$_3$ | 2-CH$_3$ | H | 115–117 | Calcd. | 68.19 | 8.58 | 4.97 | 12.58(Cl) |
| | | | | | | | | Found | 68.25 | 8.61 | 5.08 | 12.66(Cl) |
| 3 | t-C$_4$H$_9$ | Cl | CH$_3$ | CH$_3$ | 3-CH$_3$ | H | 126–128 | Calcd. | 68.19 | 8.58 | 4.97 | 12.58(Cl) |
| | | | | | | | | Found | 68.15 | 8.65 | 5.01 | 12.46(Cl) |
| 4 | t-C$_4$H$_9$ | Br | CH$_3$ | CH$_3$ | H | H | 182–183 | Calcd. | 57.70 | 7.10 | 4.49 | 25.59(Br) |
| | | | | | | | | Found | 57.87 | 7.20 | 4.59 | 25.56(Br) |
| 5 | t-C$_4$H$_9$ | Br | CH$_3$ | CH$_3$ | 2-CH$_3$ | H | 166.5–168 | Calcd. | 58.90 | 7.41 | 4.29 | 24.49(Br) |
| | | | | | | | | Found | 59.16 | 7.43 | 4.33 | 24.50(Br) |
| 6 | t-C$_4$H$_9$ | Br | CH$_3$ | CH$_3$ | 3-CH$_3$ | H | 156.5–157.5 | Calcd. | 58.90 | 7.41 | 4.29 | 24.49(Br) |
| | | | | | | | | Found | 58.77 | 4.45 | 4.21 | 24.53(Br) |
| 7 | t-C$_4$H$_9$ | Br | CH$_3$ | CH$_3$ | 4-CH$_3$ | H | 199–200 | Calcd. | 58.90 | 7.41 | 4.29 | 24.49(Br) |
| | | | | | | | | Found | 59.08 | 7.62 | 4.27 | 24.66(Br) |
| 8 | t-C$_4$H$_9$ | Br | CH$_3$ | CH$_3$ | 2-CH$_3$ | 5-CH$_3$ | 178.5–179.5 | Calcd. | 60.00 | 7.70 | 4.12 | 23.48(Br) |
| | | | | | | | | Found | 60.18 | 7.92 | 4.05 | 23.36(Br) |
| 9 | t-C$_4$H$_9$ | Br | CH$_3$ | CH$_3$ | 2-F | H | 168–169 | Calcd. | 54.56 | 6.41 | 4.24 | 24.40(Br) |
| | | | | | | | | Found | 54.38 | 6.50 | 4.33 | 24.11(Br) |
| 10 | t-C$_4$H$_9$ | Br | CH$_3$ | CH$_3$ | 3-F | H | 181–182 | Calcd. | 54.56 | 6.41 | 4.21 | 24.20(Br) |
| | | | | | | | | Found | 54.59 | 6.45 | 4.02 | 24.26(Br) |
| 11 | t-C$_4$H$_9$ | Br | CH$_3$ | CH$_3$ | 4-F | H | 183.5–184.5 | Calcd. | 54.56 | 6.41 | 4.21 | 24.20(Br) |
| | | | | | | | | Found | 54.62 | 6.22 | 4.08 | 24.09(Br) |
| 12 | t-C$_4$H$_9$ | Br | CH$_3$ | CH$_3$ | 2-Cl | H | 155.5–157 | Calcd. | 51.97 | 6.11 | 4.04 | 23.05(Br) 10.23(Cl) |
| | | | | | | | | Found | 51.88 | 6.05 | 3.99 | 23.13(Br) 10.31(Cl) |
| 13 | t-C$_4$H$_9$ | Br | CH$_3$ | CH$_3$ | 3-Cl | H | 172.5–174 | Calcd. | 51.97 | 6.11 | 4.04 | 23.05(Br) 10.23(Cl) |
| | | | | | | | | Found | 51.93 | 6.21 | 4.18 | 23.20(Br) 10.35(Cl) |
| 14 | t-C$_4$H$_9$ | Br | CH$_3$ | CH$_3$ | 4-Cl | H | 198–199 | Calcd. | 5197 | 6.11 | 4.04 | 23.05(Br) 10.23(Cl) |
| | | | | | | | | Found | 52.05 | 6.23 | 4.20 | 23.21(Br) 10.13(Cl) |
| 15 | t-C$_4$H$_9$ | Br | CH$_3$ | CH$_3$ | 2-Cl | 4-Cl | 168–169 | Calcd. | 47.27 | 5.29 | 3.68 | 20.96(Br) 18.60(Cl) |
| | | | | | | | | Found | 47.33 | 5.35 | 3.70 | 21.04(Br) 18.51(Cl) |
| 16 | t-C$_4$H$_9$ | Br | CH$_3$ | CH$_3$ | 2-Cl | 6-Cl | 162–163 | Calcd. | 47.27 | 5.29 | 3.68 | 20.96(Br) 18.60(Cl) |
| | | | | | | | | Found | 47.25 | 5.17 | 3.59 | 21.21(Br) 18.65(Cl) |
| 17 | t-C$_4$H$_9$ | Br | CH$_3$ | CH$_3$ | 2-Cl | 4-CH$_3$ | 157–159 | Calcd. | 53.28 | 6.43 | 3.88 | 22.15(Br) 9.83(Cl) |
| | | | | | | | | Found | 53.25 | 6.40 | 3.76 | 22.02(Br) 9.91(Cl) |
| 18 | t-C$_4$H$_9$ | Br | CH$_3$ | CH$_3$ | 3-Br | H | 171.5–172.5 | Calcd. | 46.06 | 5.41 | 3.58 | 40.86(Br) |
| | | | | | | | | Found | 45.89 | 5.40 | 3.62 | 40.98(Br) |
| 19 | t-C$_4$H$_9$ | Br | CH$_3$ | CH$_3$ | 2-OCH | H | 143–145 | Calcd. | 56.15 | 7.07 | 4.09 | 23.34(Br) |
| | | | | | | | | Found | 55.94 | 7.00 | 4.21 | 23.45(Br) |
| 20 | t-C$_4$H$_9$ | I | CH$_3$ | CH$_3$ | H | H | 200–201 | Calcd. | 50.15 | 6.17 | 3.90 | 35.32(I) |
| | | | | | | | | Found | 50.22 | 6.18 | 4.06 | 35.19(I) |
| 21 | t-C$_4$H$_9$ | I | CH$_3$ | CH$_3$ | 3-CH$_3$ | H | 175.5–177 | Calcd. | 51.48 | 6.48 | 3.75 | 34.00(I) |
| | | | | | | | | Found | 51.33 | 6.52 | 3.86 | 33.96(I) |
| 22 | C$_2$H$_5$—C(CH$_3$)(CH$_3$) | Cl | CH$_3$ | CH$_3$ | H | H | 117–118 | Calcd. | 68.19 | 8.58 | 4.97 | 12.58(Cl) |
| | | | | | | | | Found | 68.01 | 8.63 | 5.12 | 12.61(Cl) |
| 23 | C$_2$H$_5$—C(CH$_3$)(CH$_3$) | Br | CH$_3$ | CH$_3$ | H | H | 136–137 | Calcd. | 58.90 | 7.41 | 4.29 | 24.49(Br) |
| | | | | | | | | Found | 58.88 | 7.65 | 4.28 | 24.44(Br) |
| 24 | C$_2$H$_5$—C(CH$_3$)(CH$_3$) | Br | CH$_3$ | CH$_3$ | 3-CH$_3$ | H | 134–135 | Calcd. | 60.00 | 7.70 | 4.12 | 23.48(Br) |
| | | | | | | | | Found | 60.23 | 7.81 | 3.95 | 23.36(Br) |
| 25 | C$_2$H$_5$—C(CH$_3$)(CH$_3$) | I | CH$_3$ | CH$_3$ | H | H | 161–162 | Calcd. | 51.48 | 6.48 | 3.75 | 34.00(I) |
| | | | | | | | | Found | 51.29 | 6.53 | 3.91 | 34.05(I) |

TABLE 1-continued $$R_1-\underset{\underset{}{|}}{\overset{\overset{X}{|}}{CH}}-CONH-\underset{\underset{R_3}{|}}{\overset{\overset{R_2}{|}}{C}}-\underset{Z}{\overset{Y}{\underset{}{\bigcirc}}}$$

| Compound No. | R₁ | X | R₂ | R₃ | Y | Z | Melting point (°C.) | | Elementary analysis (%) C | H | N | Halogen |
|---|---|---|---|---|---|---|---|---|---|---|---|---|
| 26 | C₂H₅—C(CH₃)(C₂H₅) | Br | CH₃ | CH₃ | H | H | 131–132.5 | Calcd. Found | 60.00 59.95 | 7.70 7.51 | 4.12 3.98 | 23.48(Br) 23.47(Br) |
| 27 | n-C₃H₇—C(CH₃)(CH₃) | Br | CH₃ | CH₃ | H | H | 137.5–138.5 | Calcd. Found | 60.00 59.79 | 7.70 7.92 | 4.12 3.95 | 23.48(Br) 23.51(Br) |
| 28 | i-C₃H₇—C(CH₃)(CH₃) | Br | CH₃ | CH₃ | H | H | 136.5–138 | Calcd. Found | 60.00 60.10 | 7.70 7.82 | 4.12 4.34 | 23.84(Br) 23.22(Br) |
| 29 | n-C₄H₉—C(CH₃)(CH₃) | Br | CH₃ | CH₃ | H | H | 130–131.5 | Calcd. Found | 61.02 61.23 | 7.97 8.02 | 3.95 4.12 | 22.55(Br) 22.66(Br) |
| 30 | i-C₄H₉—C(CH₃)(CH₃) | Br | CH₃ | CH₃ | H | H | 117–118 | Calcd. Found | 61.02 60.97 | 7.97 7.82 | 3.95 4.06 | 22.55(Br) 22.58(Br) |
| 31 | t-C₄H₉ | Cl | C₂H₅ | CH₃ | H | H | 135–137 | Calcd. Found | 68.19 67.95 | 8.58 8.37 | 4.97 5.04 | 12.58(Cl) 12.66(Cl) |
| 32 | t-C₄H₉ | Br | C₂H₅ | CH₃ | H | H | 159–160 | Calcd. Found | 58.90 58.87 | 7.41 7.32 | 4.29 4.40 | 24.49(Br) 24.50(Br) |
| 33 | t-C₄H₉ | I | C₂H₅ | CH₃ | H | H | 177.5–179 | Calcd. Found | 51.48 51.33 | 6.48 6.51 | 3.75 3.47 | 34.00(I) 34.20(I) |
| 34 | t-C₄H₉ | Br | C₂H₅ | C₂H₅ | H | H | 172–173 | Calcd. Found | 60.00 60.08 | 7.70 7.71 | 4.12 4.20 | 23.48(Br) 23.46(Br) |
| 35 | t-C₄H₉ | Cl | —(CH₂)₂— | | H | H | 141–143 | Calcd. Found | 67.79 67.88 | 7.58 7.62 | 5.27 5.41 | 13.34(Cl) 13.22(Cl) |
| 36 | t-C₄H₉ | Br | —(CH₂)₂— | | H | H | 161–162.5 | Calcd. Found | 58.07 58.24 | 6.50 6.73 | 4.51 4.50 | 25.76(Br) 25.74(Br) |
| 37 | t-C₄H₉ | I | —(CH₂)— | | H | H | 178.5–180.5 | Calcd. Found | 50.43 50.29 | 5.64 5.38 | 3.92 3.78 | 35.52(I) 35.70(I) |
| 38 | C₂H₅—C(CH₃)(CH₃) | Cl | —(CH₂)₂— | | H | H | 138–139.5 | Calcd. Found | 68.68 68.77 | 7.92 8.06 | 5.01 5.05 | 12.67(Cl) 12.70(Cl) |
| 39 | C₂H₅—C(CH₃)(CH₃) | Br | —(CH₂)₂— | | H | H | 141–142 | Calcd. Found | 59.27 59.40 | 6.84 6.93 | 4.32 4.19 | 24.64(Br) 24.50(Br) |
| 40 | C₂H₅—C(CH₃)(CH₃) | I | —(CH₂)₂— | | H | H | 113–115 | Calcd. Found | 51.76 51.91 | 5.97 6.20 | 3.77 3.65 | 34.18(I) 34.01(I) |
| 41 | C₂H₅—C(CH₃)(CH₃) | Br | —(CH₂)₂— | | H | H | 110–112 | Calcd. Found | 60.36 60.51 | 7.15 7.22 | 4.14 3.94 | 23.63(Br) 23.55(Br) |
| 42 | i-C₃H₇—C(CH₃)(CH₃) | Br | —(CH₂)₂— | | H | H | 138–139 | Calcd. Found | 60.36 60.29 | 7.15 7.10 | 4.14 4.15 | 23.63(Br) 23.77(Br) |
| 43 | n-C₄H₉—C(CH₃)(CH₃) | Br | —(CH₂)₂— | | H | H | 129–131 | Calcd. Found | 61.37 61.50 | 7.44 7.31 | 3.98 4.04 | 22.68(Br) 22.75(Br) |
| 44 | t-C₄H₉ | Cl | —(CH₂)₃— | | H | H | 171–173 | Calcd. Found | 68.68 68.61 | 7.92 8.01 | 5.01 5.00 | 12.67(Cl) 12.56(Cl) |
| 45 | t-C₄H₉ | Br | —(CH₂)₃— | | H | H | 196–197.5 | Calcd. Found | 59.27 59.20 | 6.84 7.02 | 4.32 4.30 | 24.64(Br) 24.59(Br) |
| 46 | t-C₄H₉ | Br | —(CH₂)₄— | | H | H | 212–214 | Calcd. Found | 60.36 60.62 | 7.15 7.36 | 4.14 4.28 | 23.63(Br) 23.53(Br) |
| 47 | t-C₄H₉ | Br | —(CH₂)₅— | | H | H | 212.5– | Calcd. | 61.37 | 7.44 | 3.98 | 22.68(Br) |

TABLE 1-continued

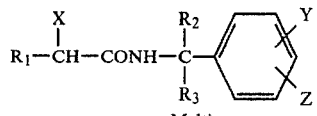

| Compound No. | R$_1$ | X | R$_2$ | R$_3$ | Y | Z | Melting point (°C.) | Elementary analysis (%) C | H | N | Halogen |
|---|---|---|---|---|---|---|---|---|---|---|---|
| | | | | | | | 213.5 | Found 61.19 | 7.56 | 3.97 | 22.46(Br) |

In the practical usage of the N-benzylhaloacetamide derivatives (I), they may be applied as such or in any preparation form such as granules, fine granules, dusts, coarse dusts, wettable powders, emulsifiable concentrates, flowable formulations, aqueous concentrates or oily suspensions.

In producing such preparation forms, solid or liquid carriers may be used. As for the solid carrier, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be given kerosene, alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone, isophorone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the N-benzylhaloacetamide derivative (I) may be usually from 0.05 to 95% by weight, preferably from 3 to 50% by weight.

Practical embodiments of the herbicidal composition according to the invention are illustratively shown in the following examples wherein parts and % are by weight.

PREPARATION EXAMPLE 1

Fifty parts of Compound No. 1, 2.5 parts of a dodecylbenzenesulfonate, 2.5 parts of a ligninsulfonate and 45 parts of diatomaceous earth are well mixed while being powdered to obtain a wettable powder.

PREPARATION EXAMPLE 2

Thirty parts of Compound No. 4, 10 parts of emulsifier ("Sorpol SM-100" manufactured by Toho Chemical Co., Ltd.) and 60 parts of xylene are well mixed to obtain an emulsifiable concentrate.

PREPARATION EXAMPLE 3

Five parts of Compound No. 37, 1 part of white carbon, 5 parts of a ligninsulfonate and 89 parts of clay are well mixed while being powdered. The mixture is then well kneaded with water, granulated and dried to obtain a granule.

PREPARATION EXAMPLE 4

Three parts of Compound No. 20, 1 part of isopropyl phosphate, 66 parts of clay and 30 parts of talc are well mixed while being powdered. The mixture is then kneaded with water, granulated and dried to obtain a granule.

PREPARATION EXAMPLE 5

Forty parts of bentonite, 5 parts of a ligninsulfonate and 55 parts of clay are well mixed while being powdered. The mixture is then well kneaded with water, granulated and dried to obtain a granule containing no active ingredient. The granule is then impregnated with 5 parts of Compound No. 7 to obtain a granule.

PREPARATION EXAMPLE 6

Ninety-five parts of bentonite of 16–48 mesh is impregnated with 5 parts of Compound No. 23 to obtain a granule.

The N-benzylhaloacetamide derivative (I) may be used together with other herbicides to improve their activity as herbicides, and in some cases, a synergistic effect may be expected. As the herbicides to be mixed therewith, there may be given phenoxy series herbicides such as 2,4-dichlorophenoxyacetic acid, 2-methyl-4-chlorophenoxyacetic acid and 2-methyl-4-chlorpheoxybutric acid (including esters and salts thereof); benzoic acid series herbicides such as 3,6-dichloro-2-methoxybenzoic acid and 2,5-dichloro-3-aminobenzoic acid; diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether; 2,4-dichlorophenyl-4'-nitro-3'-methoxyphenyl ether, 2,4-dichlorophenyl-3'-methoxycarbonyl-4'-nitrophenyl ether and sodium 5-(2'-chloro-4'-trifluoromethylphenoxy)-2-nitrobenzoate; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine and 4-amino-6-tert-butyl-3-methylthio-1,2,4-triazin-5-one; urea series herbicides such as 3-(3,4-dichlorophenyl)-1,1-dimethylurea, 3-(3,4-dichlorophenyl)-1-methoxy-1-methylurea, 1-(2,2-dimethylbenzyl)-3-p-tolylurea and 1-(2,2-dimethylbenzyl)-3-methyl-3-phenylurea; carbamate series herbicides such as isopropyl-N-(3-chlorophenyl)carbamate and methyl-N-(3,4-dichlorophenyl)-carbamate; thiolcarbamate series herbicides such as S-ethyl-N,N-dipropylthiolcarbamate, S-(4-chlorobenzyl)-N,N-diethylthiolcarbamate, S-ethyl-N,N-hexamethylene-thiolcarbamate, S-2,3-dichloroallyl-N,N-diisopropylthiolcarbamate and S-ethyl-N,N-dibutylthiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycineethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bispyridinium chloride; phosphorus series herbicides such as N-(phosphonomethyl)glycine, O-ethyl-O-(2-nitro-5-methylphenyl)-N:secbutylphosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine; aliphatic compounds series herbicides such as trichloroacetic acid, 2,2-dichloropropionic acid and 2,2,3,3-tetrafluoropropionic acid; 5-tert-butyl-3-(2,4-dichloro-5-isopropoxyphenyl)-1,3,4-oxadiazolin-2-one; 3-isopropyl-1H-2,1,3-benzothiadiazin(4)-3H-one-2,2-dioxide; 2,6-dichlorobenzonitrile; α-(β-naphthoxy)propionanilide; 4'-(phenylsulfonyl)-(1,1,1-trifluoromethylsulphono)-O-toluidide; 4-(2,4-dichlorobenzoyl)-1,3-dimethylpyrazole-5-yl-p-toluenesulfonate; N-p-chlorobenzyloxyphenyl-Δ'-tetrahydrophthalimide and the like. But, the herbicides are not of course limited to these examples.

The herbicides of the invention may be applied together with fungicides, pyrethroid series insecticides, other insecticides, plant growth regulators, fertilizers, etc.

When the N-benzylhaloacetamide derivative (I) is used as a herbicide, it may be applied before or after germination of weeds in an amount within a wide range. The amount may be usually from about 0.1 to 1 kilogram per hectare, preferably from about 0.25 to 5 kilograms per hectare.

Some test examples which show the herbicidal activity of the N-benzylhaloacetamide derivatives (I) are shown in the following Examples wherein % is by weight.

EXAMPLE I

A Wagner's pot of 14 cm in diameter was filled with 1.5 kg of paddy field soil and added with water to make paddy field conditions. Rice seedlings of 3-leaf growth stage were transplanted in the pot, and seeds of barnyard grass (*Echinochloa cruss-galli*) and *Scirpus Hotarui*, and buds of slender spikerush (*Eleocharis aciculalis*), which tided over the winter, were further sowed therein. A required amount of each test compound was applied to the soil under water-logged condition. Twenty-five days after the application, the herbicidal activity and phytotoxicity of the test compound were checked on the transplanted and sowed plants and spontaneously germinated *Monochoria vaginalis*. The results are shown in Table 2.

As to the application, a wettable powder containing a required amount of the test compound was diluted with water and applied in a proportion of 10 ml/pot by means of a pipette. The herbicidal activity was evaluated in figures ranging from 0 to 5.

| Figures | Perentage of inhibition (%) |
|---|---|
| 0 | 0–9 |
| 1 | 10–29 |
| 2 | 30–49 |
| 3 | 50–69 |
| 4 | 70–89 |
| 5 | 90–100 |

As to the evaluation of phytotoxicity, the three factors (i.e. height of plant, number of tillers and total weight (dry weight)) were each checked, and a ratio of the treated plot to the untreated plot was calculated for each factor. The phytotoxicity was evaluated based on the lowest value of the three ratios which was classified into the following grades ranging from 0 to 5.

| Grade | Ratio of the untreated plot (%) |
|---|---|
| 0 | 100 |
| 1 | 90–99 |
| 2 | 80–89 |
| 3 | 60–79 |
| 4 | 40–59 |
| 5 | 0–39 |

TABLE 2

| Compound No. | Dosage (weight of active ingredient, g/are) | Barnyard grass | *Monochoria vaginalis* | *Scirpus Hotarui* | Slender spikerush | Phototoxicity Rice plant |
|---|---|---|---|---|---|---|
| 1 | 20 | 5 | 5 | 5 | 5 | 0 |
|   | 10 | 5 | 5 | 5 | 5 | 0 |
| 2 | 40 | — | 5 | 5 | 5 | 0 |
|   | 20 | — | 5 | 5 | 4 | 0 |
| 3 | 40 | — | 5 | 5 | 5 | 0 |
|   | 20 | — | 5 | 5 | 5 | 0 |
| 4 | 20 | 5 | 5 | 5 | 5 | 0 |
|   | 10 | 5 | 5 | 5 | 5 | 0 |
| 5 | 40 | — | 5 | 5 | 5 | 0 |
|   | 20 | — | 5 | 5 | 5 | 0 |
| 6 | 40 | — | 5 | 5 | 5 | 0 |
|   | 20 | — | 4 | 5 | 5 | 0 |
| 7 | 120 | — | 5 | 5 | 5 | 0 |
|   | 80 | — | 5 | 5 | 5 | 0 |
| 8 | 40 | — | 5 | 5 | 5 | 0 |
|   | 20 | — | 5 | 5 | 4 | 0 |
| 9 | 40 | — | 5 | 5 | 5 | 0 |
|   | 20 | — | 5 | 5 | 5 | 0 |
| 10 | 20 | — | 5 | 5 | 5 | 0 |
|    | 10 | — | 5 | 4 | 5 | 0 |
| 11 | 40 | — | 5 | 5 | 5 | 0 |
|    | 20 | — | 5 | 5 | 5 | 0 |
| 12 | 40 | — | 5 | 5 | 5 | 0 |
|    | 20 | — | 5 | 5 | 5 | 0 |
| 13 | 40 | — | 5 | 5 | 5 | 0 |
|    | 20 | — | 4 | 5 | 4 | 0 |
| 14 | 120 | — | 5 | 5 | 5 | 0 |
|    | 80 | — | 5 | 5 | 5 | 0 |
| 15 | 120 | — | 5 | 5 | 5 | 0 |
|    | 80 | — | 5 | 5 | 4 | 0 |
| 16 | 120 | — | 5 | 5 | 4 | 0 |
|    | 80 | — | 5 | 5 | 4 | 0 |
| 17 | 120 | — | 5 | 5 | 5 | 0 |
|    | 80 | — | 4 | 5 | 4 | 0 |

TABLE 2-continued

| Compound No. | Dosage (weight of active ingredient, g/are) | Herbicidal activity | | | | Phototoxicity Rice plant |
|---|---|---|---|---|---|---|
| | | Barnyard grass | Monochoria vaginalis | Scirpus | Slender spikerush | |
| 18 | 120 | — | 5 | 5 | 5 | 0 |
| | 80 | — | 5 | 5 | 4 | 0 |
| 19 | 80 | — | 5 | 5 | 5 | 0 |
| | 40 | — | 5 | 5 | 5 | 0 |
| 20 | 80 | 5 | 5 | 5 | 5 | 0 |
| | 40 | 5 | 5 | 5 | 5 | 0 |
| 21 | 120 | — | 5 | 5 | 5 | 0 |
| | 80 | — | 5 | 5 | 5 | 0 |
| 22 | 20 | 5 | 5 | 5 | 5 | 0 |
| | 10 | 5 | 5 | 5 | 5 | 0 |
| 23 | 20 | 5 | 5 | 5 | 5 | 0 |
| | 10 | 5 | 5 | 5 | 5 | 0 |
| 24 | 40 | 5 | 5 | 5 | 5 | 0 |
| | 20 | 5 | 5 | 5 | 5 | 0 |
| 25 | 20 | 5 | 4 | 5 | 5 | 0 |
| | 10 | 4 | 3 | 5 | 5 | 0 |
| 26 | 20 | 5 | 5 | 5 | 5 | 0 |
| | 10 | 5 | 5 | 5 | 5 | 0 |
| 27 | 20 | 5 | 5 | 5 | 5 | 0 |
| | 10 | 5 | 5 | 5 | 4 | 0 |
| 28 | 20 | 5 | 5 | 5 | 5 | 0 |
| | 10 | 5 | 5 | 5 | 5 | 0 |
| 29 | 20 | 5 | 5 | 5 | 5 | 0 |
| | 10 | 5 | 4 | 5 | 5 | 0 |
| 30 | 20 | 5 | 5 | 5 | 5 | 0 |
| | 10 | 5 | 5 | 5 | 5 | 0 |
| 31 | 20 | 5 | 5 | 5 | 5 | 0 |
| | 10 | 5 | 5 | 5 | 5 | 0 |
| 32 | 20 | 5 | 5 | 5 | 5 | 0 |
| | 10 | 5 | 5 | 5 | 5 | 0 |
| 33 | 20 | 5 | 5 | 5 | 5 | 0 |
| | 10 | 5 | 5 | 5 | 5 | 0 |
| 34 | 40 | 5 | 5 | 5 | 5 | 0 |
| | 20 | 5 | 5 | 5 | 5 | 0 |
| 35 | 40 | 5 | 5 | 5 | 5 | 0 |
| | 20 | 5 | 5 | 5 | 5 | 0 |
| 36 | 40 | 5 | 5 | 5 | 5 | 0 |
| | 20 | 5 | 5 | 5 | 5 | 0 |
| 37 | 80 | 5 | 5 | 5 | 5 | 0 |
| | 40 | 5 | 5 | 5 | 5 | 0 |
| 38 | 80 | 5 | 5 | 5 | 5 | 0 |
| | 40 | 5 | 5 | 5 | 4 | 0 |
| 39 | 80 | 5 | 5 | 5 | 5 | 0 |
| | 40 | 5 | 5 | 5 | 5 | 0 |
| 40 | 80 | 5 | 5 | 5 | 5 | 0 |
| | 40 | 5 | 5 | 5 | 5 | 0 |
| 41 | 80 | 5 | 5 | 5 | 5 | 0 |
| | 40 | 5 | 5 | 5 | 5 | 0 |
| 42 | 80 | 5 | 5 | 5 | 5 | 0 |
| | 40 | 5 | 5 | 5 | 5 | 0 |
| 43 | 80 | 5 | 5 | 5 | 5 | 0 |
| | 40 | 5 | 5 | 5 | 5 | 0 |
| 44 | 80 | 5 | 5 | 5 | 5 | 0 |
| | 40 | 5 | 5 | 4 | 4 | 0 |
| 45 | 80 | 5 | 5 | 5 | 5 | 0 |
| | 40 | 5 | 5 | 5 | 5 | 0 |
| 46 | 80 | 5 | 5 | 5 | 5 | 0 |
| | 40 | 5 | 5 | 5 | 5 | 0 |
| 47 | 120 | 5 | 5 | 5 | 5 | 0 |
| | 80 | 5 | 5 | 5 | 5 | 0 |
| Untreated | — | 0 | 0 | 0 | 0 | 0 |

EXAMPLE II

The seeds of weeds such as large crabgrass (*Digitaria sanguinalis*), redroot pigweed (*Amaranthus retroflexus*), tubers of purple nutsedge (*Cyperus rotundus*) and seeds of crops such as soybean and cotton were each sowed in a 10 cm flower pot and covered with soil. Separately, a required amount of each test compound was formulated into an emulsifiable concentrate and diluted with water. The diluted chemical solution was applied to the soil by means of a hand sprayer and the thus treated soil was mixed and kept to the depth of 2 cm from the soil surface. Each of the weeds and crops was grown up in a green-house, and the herbicidal activity and phytotoxicity of the test compound were checked 20 days after the application. The test results are shown in Table 3. The herbicidal activity was evaluated in figures ranging from 0 to 5. The phytotoxicity to the crop plants was also indicated on the same standard as that of the herbicidal activity.

| Figures | Percentage of inhibition (%) |
|---|---|
| 0 | 0–9 |
| 1 | 10–29 |
| 2 | 30–49 |
| 3 | 50–69 |
| 4 | 70–89 |
| 5 | 90–100 |

TABLE 3

| Compound No. | Dosage (weight of active ingredient, g/are) | Herbicidal activity | | | Phytotoxicity | |
|---|---|---|---|---|---|---|
| | | Purple nutsedge | Large crabgrass | Redroot pigweed | Soybean | Cotton |
| 1 | 80 | 5 | 5 | 5 | 0 | 0 |
| | 40 | 5 | 5 | 5 | 0 | 0 |
| 2 | 80 | 5 | 5 | 5 | 0 | 0 |
| | 40 | 5 | 5 | 5 | 0 | 0 |
| 3 | 80 | 5 | 5 | 5 | 0 | 0 |
| | 40 | 5 | 5 | 5 | 0 | 0 |
| 4 | 80 | 5 | 5 | 5 | 0 | 0 |
| | 40 | 5 | 5 | 5 | 0 | 0 |
| 5 | 40 | 5 | — | — | 0 | 0 |
| | 20 | 5 | — | — | 0 | 0 |
| 6 | 40 | 5 | — | — | 0 | 0 |
| | 20 | 5 | — | — | 0 | 0 |
| 7 | 40 | 5 | — | — | 0 | 0 |
| | 20 | 5 | — | — | 0 | 0 |
| 9 | 80 | 5 | 5 | 5 | 0 | 0 |
| | 40 | 5 | 4 | 5 | 0 | 0 |
| 10 | 80 | 5 | — | — | 0 | 0 |
| | 40 | 5 | — | — | 0 | 0 |
| 11 | 80 | 5 | — | — | 0 | 0 |
| | 40 | 5 | — | — | 0 | 0 |
| 12 | 80 | 5 | — | — | 0 | 0 |
| | 40 | 5 | — | — | 0 | 0 |
| 13 | 80 | 5 | — | — | 0 | 0 |
| | 40 | 5 | — | — | 0 | 0 |
| 14 | 40 | 5 | — | — | 0 | 0 |
| | 20 | 5 | — | — | 0 | 0 |
| 15 | 80 | 5 | — | — | 0 | 0 |
| | 40 | 5 | — | — | 0 | 0 |
| 16 | 80 | 5 | — | — | 0 | 0 |
| | 40 | 5 | — | — | 0 | 0 |
| 20 | 80 | 5 | 5 | 4 | 0 | 0 |
| | 40 | 4 | 4 | 4 | 0 | 0 |
| 21 | 40 | 5 | — | — | 0 | 0 |
| | 20 | 5 | — | — | 0 | 0 |
| 22 | 80 | 5 | 5 | 4 | 0 | 0 |
| | 40 | 3 | 5 | 3 | 0 | 0 |
| 23 | 80 | 4 | 5 | 4 | 0 | 0 |
| | 40 | 3 | 5 | 3 | 0 | 0 |
| 24 | 80 | 5 | 5 | 5 | 0 | 0 |
| | 40 | 5 | 4 | 4 | 0 | 0 |
| 25 | 40 | 5 | 5 | 5 | 0 | 0 |
| | 20 | 5 | 5 | 5 | 0 | 0 |
| 26 | 80 | 5 | 5 | 4 | 0 | 0 |
| | 40 | 5 | 4 | 4 | 0 | 0 |
| 27 | 40 | 5 | 5 | 5 | 0 | 0 |
| | 20 | 5 | 4 | 4 | 0 | 0 |
| 28 | 40 | 5 | 5 | 5 | 0 | 0 |
| | 20 | 5 | 5 | 5 | 0 | 0 |
| 29 | 40 | 5 | 5 | 5 | 0 | 0 |
| | 20 | 4 | 4 | 3 | 0 | 0 |

TABLE 3-continued

| Compound No. | Dosage (weight of active ingredient, g/are) | Herbicidal activity | | | Phytotoxicity | |
|---|---|---|---|---|---|---|
| | | Purple nutsedge | Large crab-grass | Redroot pigweed | Soybean | Cotton |
| 30 | 160 | 5 | 5 | 5 | 0 | 0 |
| | 80 | 4 | 4 | 4 | 0 | 0 |
| 31 | 40 | 5 | 5 | 5 | 0 | 0 |
| | 20 | 5 | 5 | 5 | 0 | 0 |
| 32 | 40 | 5 | 5 | 5 | 0 | 0 |
| | 20 | 5 | 5 | 5 | 0 | 0 |
| 33 | 40 | 5 | 5 | 5 | 0 | 0 |
| | 20 | 5 | 5 | 5 | 0 | 0 |
| 34 | 80 | 5 | 5 | 5 | 0 | 0 |
| | 40 | 5 | 4 | 4 | 0 | 0 |
| 35 | 40 | 5 | — | — | 0 | 0 |
| | 20 | 5 | — | — | 0 | 0 |
| 36 | 40 | 5 | — | — | 0 | 0 |
| | 20 | 5 | — | — | 0 | 0 |
| 37 | 40 | 5 | — | — | 0 | 0 |
| | 20 | 5 | — | — | 0 | 0 |
| 38 | 40 | 5 | 5 | 5 | 0 | 0 |
| | 20 | 5 | 5 | 4 | 0 | 0 |
| 39 | 40 | 5 | 5 | 5 | 0 | 0 |
| | 20 | 5 | 5 | 5 | 0 | 0 |
| 40 | 40 | 5 | — | — | 0 | 0 |
| | 20 | 5 | — | — | 0 | 0 |
| 41 | 80 | 5 | — | — | 0 | 0 |
| | 40 | 5 | — | — | 0 | 0 |
| 42 | 80 | 5 | — | — | 0 | 0 |
| | 40 | 5 | — | — | 0 | 0 |
| 43 | 80 | 5 | — | — | 0 | 0 |
| | 40 | 5 | — | — | 0 | 0 |
| A*1 | 80 | 0 | 0 | 1 | 0 | 0 |
| | 40 | 0 | 0 | 0 | 0 | 0 |
| B*2 | 80 | 0 | 3 | 3 | 3 | 2 |
| | 40 | 0 | 2 | 1 | 2 | 1 |
| C*3 | 80 | 0 | 0 | 0 | 0 | 0 |
| | 40 | 0 | 0 | 0 | 0 | 0 |
| D*4 | 80 | 0 | 0 | 0 | 0 | 0 |
| | 40 | 0 | 0 | 0 | 0 | 0 |
| E*5 | 80 | 0 | 0 | 1 | 1 | 1 |
| | 40 | 0 | 0 | 0 | 0 | 0 |
| F*6 | 80 | 0 | 0 | 0 | 0 | 0 |
| | 40 | 0 | 0 | 0 | 0 | 0 |

Note:
*1 Compound disclosed in Japanese Patent Publication (unexamined) No. 88228/1973:

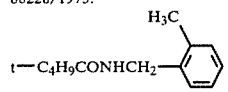

*2 Compound disclosed in U.S. Pat. No. 3,498,781:

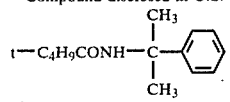

*3 Compound disclosed in J. Am. Chem. Soc., 55, 4209 (1933):

*4 Compound disclosed in U.S. Pat. No. 2,864,679:

*5 Compound disclosed in Japanese Patent publication (unexamined) No. 5005/1979:

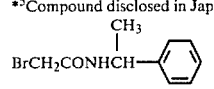

*6 Compound disclosed in Japanese Patent Publication (unexamined) No. 5005/1979:

What is claimed is:

1. A compound of the formula:

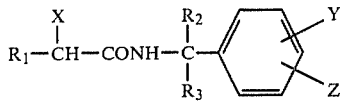

wherein $R_1$ is a $C_4$–$C_7$ tertiary alkyl group, X is a halogen atom, $R_2$ is a methyl group or an ethyl group, $R_3$ is a methyl group or an ethyl group, or when $R_2$ and $R_3$ are taken together, they represent a $C_2$–$C_5$ alkylene group, and Y and Z, which may be the same or different, are each a hydrogen, a halogen atom, a methyl group or a methoxy group.

2. The compound according to claim 1 wherein $R_1$ is a tert-butyl group or a tert-amyl group, X is a chlorine atom, a bromine atom or an iodine atom, $R_2$ is a methyl group or an ethyl group, $R_3$ is a methyl group, or when $R_2$ and $R_3$ are taken together, they represent a $C_2$ alkylene group, Y is a hydrogen atom, a methyl group or a chlorine atom and Z is a hydrogen atom.

3. The compound according to claim 1 which is

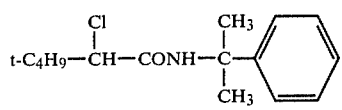

4. The compound according to claim 1 which is

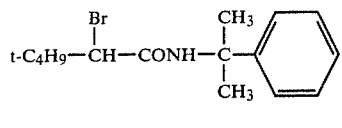

5. The compound according to claim 1, which is

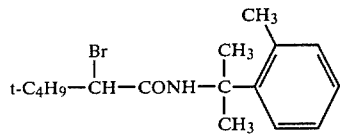

6. The compound according to claim 1 which is

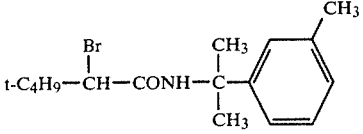

7. The compound according to claim 1 which is

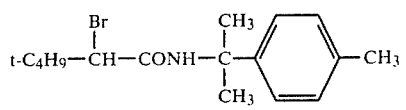

8. The compound according to claim 1, which is

9. The compound according to claim 1, which is

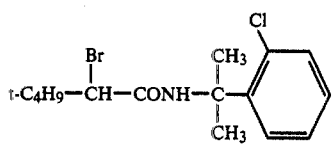

10. The compound according to claim 1, which is

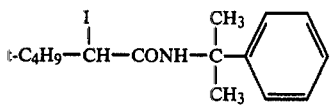

11. The compound according to claim 1, which is

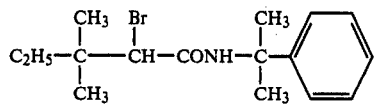

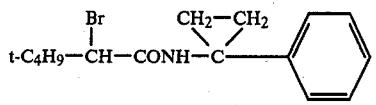

12. A herbicidal composition comprising an inert carrier or diluent and at least one of the N-benzylhaloacetamide derivatives according to claim 1 as an active ingredient in a herbicidally effective amount.

13. A method for controlling weeds which comprises contacting the weeds with an effective amount of at least one of the N-benzylhaloacetamide derivatives according to claim 1.

* * * * *